United States Patent [19]

Kubota et al.

[11] Patent Number: 4,820,744

[45] Date of Patent: Apr. 11, 1989

[54] COMPOSITIONS FOR DENTAL RESTORATION

[75] Inventors: Takao Kubota, Kamakura; Tetsuro Sakuma; Ryoji Nakazato, both of Tokorozawa, all of Japan

[73] Assignee: G-C Dental Industrial Corp., Tokyo, Japan

[21] Appl. No.: 32,626

[22] Filed: Apr. 1, 1987

[30] Foreign Application Priority Data

Apr. 18, 1986 [JP] Japan ................................ 61-88161

[51] Int. Cl.$^4$ .......................... C08F 2/50; A61K 6/08
[52] U.S. Cl. ...................................... 522/13; 522/14; 522/21; 522/24; 522/77; 522/83; 522/95; 522/96; 522/120; 522/121; 522/908; 523/116
[58] Field of Search ...................... 522/13, 908, 14, 21, 522/24, 83, 95, 96, 77, 120, 121; 523/116

[56] References Cited

U.S. PATENT DOCUMENTS

| | | | |
|---|---|---|---|
| 4,271,258 | 6/1981 | Watariguchi | 430/286 |
| 4,286,008 | 8/1981 | Reed | 428/195 |
| 4,596,147 | 5/1986 | Lindley | 430/286 |
| 4,674,980 | 6/1987 | Ibsen | 522/13 |

OTHER PUBLICATIONS

European Search Report–United Kingdom Dated Jun. 16, 1987.

*Primary Examiner*—John C. Bleutge
*Assistant Examiner*—David Buttner
*Attorney, Agent, or Firm*—Oblon, Fisher, Spivak, McClelland & Maier

[57] ABSTRACT

A combined chemical-light-polymerization type composition for dental restoration consists of a formulation A composed mainly of a. an ethylenically polymerizable unsaturated compound, b. a photopolymerization initiator and c. a reducing agent, and a formulation B composed mainly of d. a filler and e. an organic peroxide. The formulations A and B are separately packaged and designed to be mixed for use.

14 Claims, No Drawings

COMPOSITIONS FOR DENTAL RESTORATION

BACKGROUND OF THE INVENTION

1. Field of the Invention

The present invention relates to a composition for dental restoration which takes the advantages of both light-polymerization and chemical polymerization, and which is well cured by the irradiation of visible lights in a short period of time with no fear that it may be adversely affected by the intensity of light due to the transmission properties or transmission depth of light.

2. Statement of the Prior Art

Heretofore, the so-called chemical polymerization and light polymerization type restoration materials have been widely used in dentistry. The chemical polymerization type restoration materials are broken down into the powder•liquid type and the paste•paste type. Generally, the powder•liquid type restoration materials comprise a powdery component in which an organic peroxide such as benzoyl peroxide is added to a powdery organic such as polymethyl methacrylate and a powdery inorganic such as silica, and a liquid component in which N,N'-dimethyl-p-toluidine and the like is added to a polyfunctional monomer such as methyl methacrylate and/or dimethacrylate and/or trimethacrylate. In use, when the powder and liquid components are mixed together, the monomer is polymerized and cured by the oxidation-reduction reaction between the organic peroxide and the amine. On the other hand, the paste•paste type restoration materials are in the form of a paste composed mainly of fine powders and a binder resin for bonding together the powders. That paste is divided into two portions, one portion containing an organic peroxide and the other portion, an amine. In use, such pasty portions are mixed together, and the resulting mixture is filled in a cavity. Thereafter, the binder resin is polymerized and cured by the oxidation-reduction reaction between the organic peroxide and the amine within a certain period of time.

The disadvantage of the restoration materials of such types is that since the curing time is predetermined regardless of the will of an operator, it is required for the operator to rapidly finish his or her filling manipulation, when the predetermined curing time is short. In some cases, it is likely that the restoration materials may be cured before the filling manipulation is finished. It has also been pointed out that when the predetermined curing time is long, the physical properties of the restoration materials are adversely affected as a result of the fact that they are exposed to moisture or sputum in the oral cavity, while not cured. When it is intended to effect curing within a shorter period of time, it is required that the amount of the catalyst added such as an organic peroxide or amine be increased. Increases in the amount of the organic peroxide or amine added are practically unpreferred in dentistry, since coloration and discoloration tendencies become more marked and the amount of heat generated become more increased, correspondingly, and this is by no means preferred in practical dentistry. It has also have been pointed out that in the case of low-temperature polymerization or thin-layer polymerization, the polymerization reaction becomes incomplete, thus yielding an uncured mass having poor physical properties.

Turning to the light polymerization type restoration materials in which a photo-polymerization catalyst is used in lieu of the organic peroxide-amine base catalyst in the chemical polymerization type, their curing reaction does not proceed, unless they are exposed to light. This leads to the advantages that the manipulation and time therefor are optimized, because it is possible to substantially control the manipulation time and curing time according to the operator's will. Thus, the light polymerization type restoration materials have recently found increased use in dentistry.

A number of the compositions for the light polymerization type of dental restoration materials are well-known in the art. In view of their safe use in the oral cavity, however, use is often made of the visible light polymerization type restoration materials in particular. Compositions relating to the method using the light curing catalysts disclosed in British Pat. No. 1408265 specification, i.e., the α-diketone base camphor quinone and amine reducing agents are used in virtually all products. The visible light curing type restoration materials are cured upon exposure to light falling under the wavelength range of 400 to 500 nm, but do not provide any satisfactory cured product in a wavelength region of below 400 nm.

The disadvantages of the light polymerization type restoration materials are that their curing reaction is easily affected by the transmission properties and intensity of light, and becomes insufficient, as the portion to be irradiated is far away from the light source used, or the transmission properties drop, leaving a large amount f residual unreacted monomer. There are thus drops in the physical properties such as hardness, strength and the like, which are unpreferred from the clinical point-of-view. When the material is opacified by the addition of an opaque component and the like, it is cured only on the outer layer, and is not possible to be set deep inside. These light-polymerizable compositions for dental use are typically disclosed in our co-pending U.S. application Ser. Nos. 906,196, 906,283 and 906,285 filed on 9/11/96, now U.S. Pat. No. 4,771,084.

SUMMARY OF THE INVENTION

In consequence of intensive and extensive studies made of the compositions for dental restoration materials which excel in curing property, manipulation property and storage stability, provide cured products having improved properties, and are free from the disadvantages of the conventional compositions for dental restoration materials, it has been found that such compositions are obtained by chemical/light polymerization combinations and separately packaged. It has further been found that the light curing property of the light polymerization system is promoted by the chemical polymerization system of an organic peroxide.

In short, the present invention provides a combined chemical/light-polymerization type composition for dental restoration compositions consisting of a formulation A composed mainly of a. an ethylenically polymerizable unsaturated compound, b. a photo-polymerization initiator and c. a reducing agent, and a formulation B composed mainly of d. a filler and e. an organic peroxide, said formulations A and B being separately packaged and designed to be mixed for use.

Owing to their reduced or limited content of residual unpolymerized monomer, the cured products obtained from the compositions according to the present invention excel in the physical properties such as hardness, strength and the like, and can provide dental prostheses which are improved in respect of their curing property without giving any irritation to the oral mucosa and the dental pulp. Since the organic peroxide is packaged separately from the polymerizable compound, it excels in storage stability with no fear of curing and deterioration during storage.

The compositions according to the present invention can be widely used as the materials for prosthesis, operative dentistry, periodontics, orthodonntics and other dental techniques such as those represented by fillings, facings, jacket crowns, temporary crowns, inlays, bite checks, artificial tooth, denture bases, repairments, rebases, trays, base plates, patterns, orthodontic denture bases, separators and pyorrheal teeth fixtures.

The constitutional component a in the compositions of the present invention, i.e., the ethylenically polymerizable unsaturated compound refers to that having in its chemical structure at least one ethylenically unsaturated double-bond, and taking on the chemical form of a monomer, prepolymer (viz., a dimer, trimer and other oligomer) or a mixutre or copolymer thereof.

Specifically speaking, the monomers having therein one ethylenically unsaturated double-bond include methyl methacrylate, ethyl methacrylate, isopropyl methacrylate, isobutyl methacrylate, propyl methacylate, benzyl methacrylate, hydroxyethyl methacrylate, tetrahydrofurfuryl methacrylate and glycidyl methacrylate and acrylates thereof. The monomers having therein two ethylenically unsaturated double-bonds are broken down into aromatic ones including 2,2-bis(methacryloxyphenyl)propane, 2,2-bis[4-(2-hydroxy-3-methacryloxyphenyl)]propane, 2,2-bis(4-metharyloxyethoxyphenyl)propane, 2,2-bis(4-methacryloxydiethoxyphenyl)propane and 2,2-bis(4-methacryloxypropoxyphenyl)propane, 2,2-bis(4-methacryloxypolyethoxyphenyl)propane and acrylates thereof and aliphatic ones including ethylene glycol dimethacrylate, diethylene glycol dimethacrylate, triethylene glycol dimethacrylate, butylene glycol dimethacrylate, neopentylglyocl dimethacrylate, 1,3-butanediol dimethacrylate, 1,4-butanediol dimethacrylate, 1,6-hexanediol dimethacrylate and dimethacryloxyethyltrimethylhexamethylene dicarbamate and acrylates thereof. The monomers having therein three ethylenically unsaturated double-bonds include trimethylolpropane trimethacrylate, trimethylolethane trimethacrylate, pentaerythritol trimethacrylate and trimethylolmethane trimethacrylate and acrylates thereof. The monomers having therein four ethylenically unsaturated double-bonds include pentaerythritol tetramethacrylate and tetracrylate as well as the urethane base monomers expressed in terms of the following structural formulae.

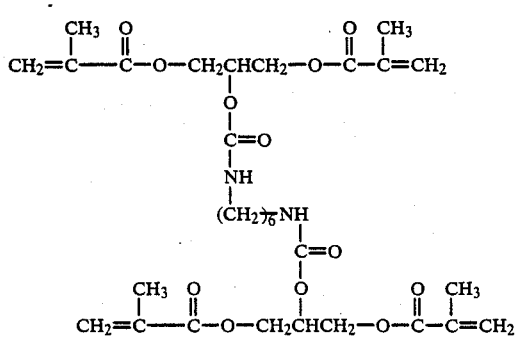

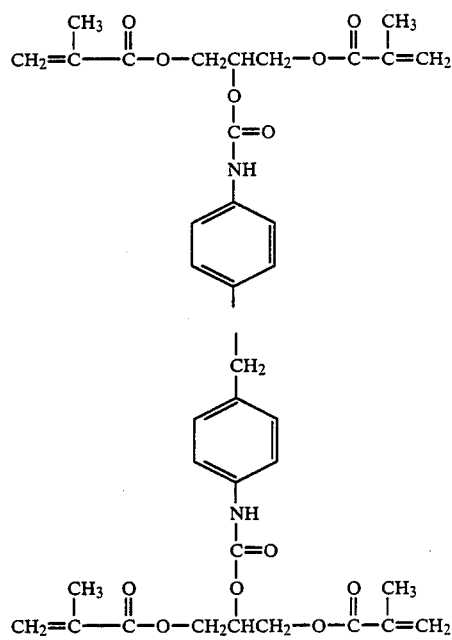

In addition, the compounds containing carboxyl groups may be used, including acrylate oligomers of 4-methacryloxyethyltrimellitic acid and its anhydride, acryloxyethyl phthalic acid, acryloxyethyl succinic acid and the like. Use may also be made of polyacrylic copolymers. These acrylates and methacrylates may be used alone or in combination.

Preferably, these ethylenically polymerizable unsaturated compounds should be applied in a quantitive range of 90 to 10 weight % with respect to the filler used. When such compounds depart from the aforesaid range, any satisfactory formation of the dental restoration materials is not achieved.

The first constitutional component used as the photopolymerization intiator b is a ketal base compound expressed in terms of the following formula 1:

$$X-A-\underset{\underset{O}{\|}}{\overset{\overset{OR}{|}}{C}}-\underset{\underset{OR}{|}}{\overset{}{C}}-A-X \quad [1]$$

wherein

X is H, Cl, an alkyl group having 1 to 5 carbon atoms or an alkoxy group having 1 to 5 carbon atoms, A is a six-membered aromatic group, and R is an alkyl group having 1 to 10 carbon atoms, an aralkyl group having 7 to 9 carbon atoms or a

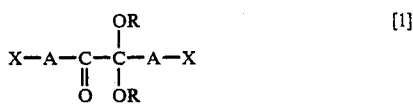

in which n is an integer of 2 to 5, m is an integer of 1 to 5 and R' is an alkyl group having 1 to 5 carbon atoms. For instance, the ketal base compounds include, in addition to one having the following formula:

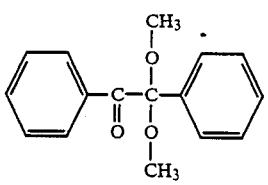

benzil diethyl ketal, benzil dipropyl ketal, benzil-di(β-phenylethyl)ketal, benzil-di(2-methoxyethyl)ketal, benzil-di(2-ethoxyethyl)ketal, benzil-di(2-methoxyethoxyethyl)ketal, benzil-di(2-ethoxyethoxyethyl)ketal, 4,4'-dimethylbenzil-dimethyl ketal, 2,2'-dimethoxybenzil-diethyl ketal, 4,4'-dichlorobenzil-diethyl ketal, 4,4'-dichlorobenzil-dipropyl ketal and so on. Among them, particular preference is given to benzil dimethyl ketal, benzil diethyl ketal, benzil-di(2-methoxyethyl)ketal and 4,4'-dimethylbenzil-dimethyl ketal.

The second constitutional component in the photo-polymerization initiator is an anthraquinone base compound expressed in terms of the following general formula 2:

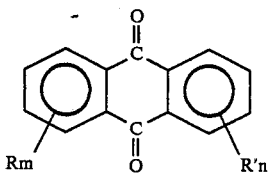

[2]

wherein

R and R' each represent a lower alkyl group, a substituted alkyl group, an alkoxy group, a halogen atom, a nitro group or a divalent unsaturated group forming a condensation ring structure, and m and n each denote 0 or an integer of 1 to 4. The anthraquinone base compound includes anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone and so on. Among them, particular preference is given to anthraquinone, 1-chloroanthraquinone and 1,2-benzanthraquinone. These photo-polymerization initiators may be used alone or in combination thereof.

Referring to the amounts of the aforesaid ketal and anthraquinone base photo-polymerization initiators added, it is preferred that the former is added in an amount of 0.01 to 5 weight % relative to the compound having at least one ethylnenically unsaturated double-bond, while the latter is added in an amount of 0.01 to 5 weight % relative thereto. In ranges departing from those as mentioned just above, the resulting curing property and color stability are practically unsuitable for use in dentistry.

The third constitutional component in the photo-polymerization initiator is thioxanthone base compound having the following general formula 3:

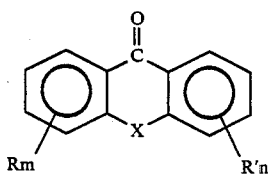

[3]

wherein

X is >S, >SO and >SO$_2$,

R and R' each independently are a lower alkyl group, a substituted alkyl group, a divalent unsaturated group bonded to the adjacent position of the aforesaid formula 3 to form a condensation ring structure, an alkoxy group, a halogen atom or a nitro group, and m and n each represent independently 0 or an integer of 1 to 4. The thioxanthone base compound includes thioxanthone, 2-chlorothioxanthone, 2-isopropylthioxanthone, 2-nitorthioxanthone, 2-methylthioxanthone, 2,4-dimethylthioxanthone, 2,4-diethylthioxanthone, 2,4-diisopropylthoxanthone, 2-chloro-7-trifluoromethylthioxanthone, thioxanthone-10,10-dioxide, thioxanthone-10-oxide and so on. Among them, preference is given to thioxanthone, 2-chlorothioxanthone, 2,4-diethylthioxanthone and 2,4-disopropylthioxanthone. These photo-polymerization initiators may be used alone or in combination thereof. Preferably, the aforesaid ketal and thioxanthone base compounds each should be added to the ethylenically polymerizable unsaturated compounds in a quantitative range of 0.01 to 5 weight %. In ranges departing from those as mentioned just above, the resulting curing property and color stability are practically unsutable for use in dentistry.

The fourth constitutional component in the photo-polymerization initiator is a benzoin alkyl ether having the following general formula 4:

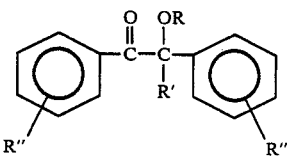

[4]

wherein

R is an alkyl group,

R' is selected from the group consisting of a hydrogen atom, an alkyl group, a halogen atom and an alkoxy group, and R'' is one or more groups which may optionally be present on the respective henyl rings of that formula, and are selected from the group consisting of an alkyl group, an alkoxy group, a halogen atom and an alkylamino group. The benzoin alkyl ether base compound include benzoin methyl ether, benzoin ethyl ether, benzoin isopropyl ether, benzoin-n-butyl ether, benzoin isobutyl ether and so on. Among them, benzoin isobutyl ether is particularly preferred. These photo-polymerization initiators may be used alone or in combination thereof. Preferably, these photo-polymerization initiators should be added to the ethylenically polymerizable unsaturated compounds in an amount of 0.01 to 5 weight %. In ranges departing from those as mentioned just above, the resulting curing property and color stability are practically unsuitable for use in dentistry.

As the photo-polymerization initiators use may further be effectively made of α-diketone base compounds, camphor quinone, benzil, diacetyl, acenaphthenquinone and 9,10-phenanthrenequionone. Among them, camphor quinone and benzyl are particularly preferred. These photo-polymerization initiators may be used alone or in combination thereof.

The α-diketone base compounds should preferably be used in an amount of 0.01 to 5 weight % relative to the ethylenically polymerizable unsaturated compounds. In ranges departing from those as mentioned just above, the resulting curing property and color stability are practically unsuitable for use in dentistry.

The α-diketone base compounds may be used in the form of mixtures with the aforesaid ketal-anthraquinone, ketal-thioxanthone and ketal-benzoin alkyl ether base compounds.

As the constitutional component of the reducing agents c of the present invention, use is made of compounds which are capable of reducing photosensitizers, when they are excited, but are incapable of reducing them, when they are not excited by active energy beams. The reducing agents may be primary, secondary or tertiary amines. In the amine

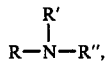

none of R, R' and R" may be a hydrogen atom, or one or two of R, R' and R" may be a hydrogen atom. One or more groups of R, R' and R" may be different or identical hydrocarbon groups. For instance, the hydrocarbon groups may be alkyl, cycloalkyl, hydroxyalkyl or aralkyl groups. Preferred R, R' and R" are $C_1$–$C_{10}$ alkyl groups.

Suitable examples of the reducing agents wherein one or more groups represented by R, R' and R" are hydrocarbons include propylamine, n-butylamine, pentylamine, hexylamine, dimethylamine, diethylamine, dipropylamine, di-n-butylamine, dipentylamine, 2-dimethylamino ethanol, trimethylamine, triethylamine, tripropylamine, tri-n-butylamine, tripentylamine, dimethylaminoethyl methacrylate, diethylaminoethyl methacrylate, triethanolamine, and long-chain aliphatic amines.

Examples of the reducing agents containing an aromatic group include N,N'-dimethylaniline, N,N'-dimethyl-p-toluidine, p-tolyldiethanolamine, m-tolyldiethanolamine, N-methyldiphenylamine, 2-dimethylaminobenzoic acid ethyl ester, 4-dimethylaminobenzoic acid ethyl ester, 4-dimethylaminobenzoic acid methyl ester, 4-dimethylaminobenzoic acid butyl ester, 4-dimethylaminobenzoic acid 2-ethylhexyl ester, 4-dimethylaminobenzoic acid isoamyl ester.

Use may be made of a diamine having the following structure:

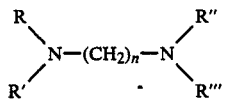

wherein n is an integer of 2 or higher, and different or identical groups R, R', R" and R'" are hydrogen atoms or hydrocarbon groups, particularly alkyl groups. This type of reducing agent may be exemplified by ethylenediamine, trimethylenediamine, tetramethylenediamine, pentamethylenediamine or hexamethylenediamine or N-hydrocarbon derivatives, especially N-alkyl derivatives.

Examples of the reducing agents in which an element N forms a part of ring includes, for instance, piperidine and N-hydrocarbon derivatives thereof.

Other reducing agents which may be used in the present invention include triaryl amines, allyl thiourea, aromatic sulfinates, 5-alkyl or 5-aryl-barbituric acid and so on.

Among these reducing agents, preference is given to dimethylaminoethyl methacrylate, triethanolamine, 4-dimethylaminobenzoic acid methyl ester and 4-dimethylaminobenzoic acid ethyl ester.

The concentration of these reducing agents should preferably 0.1 to 5 weight % based on the ethylenically polymerizable unsaturated compounds in view of dental color stability and curing property.

The constitutional components of the filler d may be based on inorganics, organics or admixtures thereof. Suitable examples of fillers include inorganic fillers such as powdery quartz, powdery alumina, powdery glass, kaolin, talc, calcium carbonate, barium aluminosilicate glass, titanium oxide, borosilicate glass and powdery colloidal silica as well as the so-called organic composite filler obtained by compacting colloidal silica with a polymer, followed by pulverization. The powdery polymers used to this end include polymethyl acrylate, polymethyl methacrylate, polyethyl methacrylate, copolymer of methyl methacrylate with ethyl methacrylate, crosslinked type polymethyl methacrylate and copolymer of ethylene with vinyl acetate. The polymer powders may be used in the form of mixtures with the aforesaid inorganic powders.

It is preferred that, prior to mixing the inorganic filler with the binder resin, that filler is treated on its surface with a coupling agent capable of reacting with both. The coupling agents used for this purpose may include silane coupling agent, titanate coupling agent, aluminate coupling agent and so on. Alternatively, the inorganic filler may be grafted on its surface for bonding to the binder resin.

The silane copling agents used are exemplified by γ-methacryloxypropyl trimethoxysilane, vinyltrichlorosilane, vinyltris(β-methoxyethoxy)silane, γ-methacryloxypropylmethyldimethoxysilane, γ-glycidoxypropyl trimethoxysilane, γ-chloropropyl trimethoxysilane, β-(3,4-epoxycyclohexyl)ethyl trimethoxysilane, trimethylchlorosilane, dimethyldichlorosilane, hexamethyldisilane, γ-aminopropyl triethoxysilane, N-β-(aminoethoxy)-γ-aminopropyl trimethoxysilane, γ-urenoidopropyl trimethoxysilane and so on.

In the present invention, any method for surface treatment with these coupling agents may be used. The amount of said surface treatment agents to be used varies depending upon the nature and state required, and is not unconditionally predetermined. Generally, it is desired, however, that said surface treatment agents may be used in an amount ranging from 0.1 to 20 weight %, preferably 1 to 10 weight %.

The organic peroxides that are the constitutional component e are expressed in terms of R—O—O—R' wherein R and R' may be different or identical, and each indicates a hydrogen atom, an alkyl group, aryl group or an acyl group. Suitable examples of the organic peroxides include acetyl peroxide, cumene hydroperoxide, benzoyl peroxide, di-t-butyl peroxide, dilauroyl peroxide, t-butyl perbenzoate, and the like.

It is preferred that the concentration of these organic peroxides may be 0.1 to 5 weight % based on the ethylenically polymerizable unsaturated compound in view of dental color stability and curing property.

It is noted that in addition to the aforesaid constitutional components, usually employed polymerization inhibitors and ultraviolet light absorbers may be used, if required.

The active energy beams used in the present invention may be visible light or ultraviolet light, or may include in their spectra both visible and ultraviolet light. The light sources applicable to the compositions of the present invention include carbon arc, mercury lamps, xenon lamps, metal halide lamps, fluorescent lamps, tungsten lamps and argon ion laser.

In the following, the present invention will be explained in further detail with reference to the examples to which the present invention is to be not limited.

EXAMPLE 1

In use a formulation A obtained by mixing together 70 grams of a methyl methacrylate monomer and 30 grams of aliphatic urethane dimethacrylate used as the polymerizable compounds having an ethylenically unsaturated double-bond, 0.5 and 0.05 grams of benzil dimethyl ketal and 1.2-benzanthraquinone as the photo-polymerization initiators and 0.5 grams of dimethylaminoethyl methacrylate as the reducing agent was blended at room temperature with a formulation B obtained by mixing 200 grams of a methyl methacrylate polymer used as the filler with 1.0 gram of benzoyl peroxide as the organic peroxide to form a plastic paste. A stainless mold was provided therethrough with a round hole of 4 mm in diameter and 10 mm in thickness, in which the paste was filled, followed by covering the surface thereof with cellophane paper. The assembly was then exposed to visible light for 30 seconds with a device (with Luxor-trade name-manufactured by ICI). After the cylindrical sample had immediately been taken out of the mold and unpolymerized matters had been removed, its vertical length was measured to determine the depth of curing achieved by 30-seconds exposure. Another sample allowed to stand alone for 5 minutes after 30-seconds exposure was measured in respect of its vertical length in a similar manner to determine the depth of curing after the lapse of 5 minutes. Measurement was also made of the hardness of the surface and 3 mm-deep portions of the sample permitted to stand alone for 5 minutes. The samples, whose depth of curing was measured were exposed to sunlight for 48 hours for comparison with an unexposed sample in respect of discoloration.

For bending strength testing, the aforesaid paste was then filled in a stainless mold (2 mm×2 mm×25 mm), followed by covering the surface thereof with cellophane paper. Thereafter, the assembly was uniformly exposed to visible light for 30 seconds (with Luxor—trade name—manufactured by ICI). Immediately after letting alone for 5 minutes, the sample was removed for measurement of its bending strength.

For storage testing, the formulations for use were let alone for one month in a constant-temperature chamber at 45° C. to observe them. The results are set forth in the Table to be given later.

Such results have confirmed that the addition of the organic peroxide permits the invented compositions to be cured to a larger depth, even when the irradiation time is as short as 30 seconds, and that the addition of only a small amount of the reducing agent allows the invented compositons to be completely cured as a whole after the lapse of 5 minutes. It has also been ascertained that the invented compositions undergo no substantial discoloration from the fact that the amount of the reducing agent added is small, and has shown satisfactory storage stability. The bending strength obtained is also high.

Also similar results have been ascertained in the following examples.

EXAMPLES 2-3

Except that the photo-polymerization initiators, reducing agents and organic peroxides as specified in the table were used in the amounts specified therein, the procedures of Example 1 were repeated to examine various compositions in respect of their depth of curing, bending strength, discoloration, hardness and storage stability. The results are set forth in the table.

EXAMPLES 4-6

Except that 70 grams of an ethyl melthacrylate monomer and 30 grams of an aliphatic urethane diacrylate, and 200 grams of a methyl methacrylate polymer were used as the polymerizable compounds having an ethylenically unsaturated double-bond and the filler, respectively, photo-polymerization initiators, reducing agents and organic peroxides as specified in the table were used in the amounts specified therein, the procedures of Example 1 were repeated to examine various compositions in respect of their depth of curing, bending strength, discoloration, hardness and storage stability. The results are set forth in the table.

EXAMPLES 7-9

Except that 70 grams of 2,2-bis[4-(2-hydroxy-3-methacryloxyphenyl)]propane and 30 grams of triethylene glycol dimethacrylate, and 100 grams of finely divided silica surface-treated with 5 grams of γ-methacryloxypropy trimethoxysilane were used as the polymerizable compounds and the filler, respectively, and that the photo-polymerization initiators, reducing agents and organic peroxides as specified in the table were used in the amounts specified therein, the procedures of Example 1 were repeated to examine various compositions in respect of their depth of curing, bending strength, discoloration, hardness and storge stability. The results are set forth in the table.

EXAMPLE 10

Except that 50 grams of an aliphatic urethane dimethacrylate and 50 grams of trimethylolpropane triacrylate, and 30 grams of finely divided titanium oxide and 70 grams of finely divided alumina oxide, each surface-treated with 5 grams of γ-methacryloxypropyl trimethoxysilane, were used as the polymerizable compounds having an ethylenically unsaturated double-bond and the fillers, and that the photo-polymerization initiators, reducing agents and organic peroxide as specified in the table were used in the amounts specified therein, the procedures of Example 1 were repeated to examine the compositions in respect of its depth of curing, bending strength, discoloration, hardness and storage stability. The results are set forth in the table.

EXAMPLE 11

Except that 100 grams of a methyl methacrylate monomer and 200 grams of a methyl methacrylate polymer were used as the the polymerizable compound having an ethylenically unsaturated double-bond and the filler, respectively, and that the photo-polymerization initiators, reducing agents and organic peroxide as specified in the table were used in the amount specified therein, the procedures of Example 1 were repeated to examine the composition in respect of its depth of curing, bending strength, discoloration, hardness and storage stability. The results are set forth in the table.

EXAMPLE 12

Except that 100 grams of a methyl methacrylate monomer and 200 grams of a methyl methacrylate polymer were used as the the polymerizable compound having an ethylenically unsaturated double-bond and the filler, respectively, and that the photo-polymerization initiators, reducing agent and organic peroxide as specified in the table were used in the amounts specified therein, the procedures of Example 1 were repeated to examine the composition in respect of its depth of curing, bending strength, discoloration, hardness and storage stability. The results are set forth in the table.

EXAMPLE 13

Except that 70 grams of a methyl acrylate monomer and 30 grams of an aliphatic urethane dimethacrylate, and 200 grams of a methyl methacrylate polymer were used as the polymerizable compounds having an ethylenically unsaturated double-bond and the filler, respectively, and that the photo-polymerization initiators, reducing agent and organic peroxide as specified in the table were used in the amounts specified therein, the procedures of Example 1 were repeated to examine the composition in respect of its depth of curing, bending strength, discoloration, hardness and storage stability. The results are set forth in the table.

EXAMPLE 14

Except that 100 grams of 2,2-bis(4-methacryloxypolyethoxyphenyl)propane and 200 grams of a methyl methacrylate polymer were used as the polymerizable compound having an ethylenically unsaturated double-bond and the filler, respectively, and that the photo-polymerization inititor, reducing agent and organic peroxide as specified in the table were used in the amounts as specified therein, the procedures of Example 1 were repeated to examine the composition in respect of its depth of curing, bending strength, discoloration, hardness and storage stability. The results are set forth in the table.

EXAMPLE 15

Except that 100 grams of an aliphatic urethane diacrylate and a product obtained by heat-setting and pulverizing a mixture of 50 grams of finely divided silica with 50 grams of trimethylolpropane trimethacrylate were used as the polymerizable compound having an ethylenically unsaturated double-bond and the filler, respectively, and that the photo-polymerization initiators, reducing agents and organic peroxide as specified in the table were used in the amount as specified therein, the procedures of Example 1 were repeated to examine the composition in respect of its depth of curing, bending strength, discoloration, hardness and storage stability. The results are set forth in the table.

EXAMPLE 16

Except that 70 grams of a methyl methacrylate monomer and 30 grams of an aliphatic urethane diacrylate and 200 grams of a methyl/ethyl methacrylate copolymer were used as the polymerizable compounds having an ethylenically unsaturated double-bond and the filler, and that the photo-polymerization initiators, reducing agent and organic peroxide as specified in the table were used in the amount as specified therein, the procedures of Example 1 were repeated to examine the composition in respect of its depth of curing, bending strength, discoloration, hardness and storage stability. The results are set forth in the table.

EXAMPLE 17

Except that 100 grams of trimethylolpropane trimethacrylate and 200 grams of a methyl/ethyl methacrylate copolymer were used as the polymerizable compound having an ethylenically unsaturated double-bond and the filler, respectively, and that the photo-polymerization initiators, reducing agent and organic peroxide as specified in the table were used in the amount as specified therein, the procedures of Example 1 were repeated to examine the composition in respect of its depth of curing, bending strength, discoloration, hardness and storage stability. The results are set forth in the table.

EXAMPLE 18

Except that 50 grams of isobutyl methacrylate monomer and 50 grams of methyl acrylate monomer, and 200 grams of a methyl/ethyl methacrylate copolymer were used as the polymerizable compound having an ethylenically unsaturated double-bond and the filler, respectively, and that the photo-polymerization initiator, reducing agent and organic peroxide as specified in the table were used in the amount as specified therein, the procedures of Example 1 were repeated to examine the composition in respect of its depth of curing, bending strength, discoloration, hardness and storage stability. The results are set forth in the table.

EXAMPLE 19

Except that 35 grams of methyl methacrylate monomer, 35 grams of methyl acrylate monomer and 30 grams of an aliphatic urethane dimethacrylate, and 200 grams of a methyl methacrylate polymer were used as the polymerizable compounds having an ethylencially unsaturated double-bond and the filler, respectively, and that the photo-polymerization initiators, reducing agent and organic peroxide as specified in the table were used in the amount as specified therein, the procedures of Example 1 were repeated to examine the composition in respect of its depth of curing, bending strength, discoloration, hardness and storage stability. The results are set forth in the table.

EXAMPLE 20

Except that 30 grams of isobutyl methacrylate monomer, 30 grams of methyl methacrylate monomer, 10 grams of trimethylolpropane trimethacrylate and 30 grams of an aliphatic urethane diacrylate, and 200 grams of a methyl/ethyl methacrylate copolymer were used as the polymerizable compounds having an ethylenically unsaturated double-bond and the filler, respectively, and that the photo-polymerization initiators, reducing agents and organic peroxide as specified in the table were used in the amount as specified therein, the procedures of Example 1 were repeated to examine the composition in respect of its depth of curing, bending strength, discoloration, hardness and storage stability. The results are set forth in the table.

Comparison Example 1

In use, a formulation A obtained by mixing together 70 grams of a methyl methacrylate monomer and 30 grams of an aliphatic urethane dimethacrylate used as the polymerizable compounds having an ethylenically unsaturated double-bond with 0.5 grams of p-tolyldiethanol amine as the reducing agent as blended at room temperature with a formulation B obtained by mixing 200 grams of a methyl methacrylate polymer used as the filler with 1.0 gram of benzoyl peroxide as the organic peroxide to form a plastic paste.

In accordance with the procedures of Example 1, the paste was then measured in respect of its depth of curing, bending strength, discoloration, hardness and storage stability. The results are set forth in the table.

Comparison Example 2

As an example of the chemical polymerization type heretofore used in the prior art, a formulation A obtained by mixing 70 grams of a methyl methacrylate monomer and 30 grams of an aliphatic urethane dimethacrylate used as the polymerizable compounds having an ethylenically unsaturated double-bond with 1.5 grams of p-tolyldiethanol amine as the reducing agent was blended at room temperature in use with a formulation B obtained by mixing 200 grams of a methyl methacrylate polymer used as the filler with 1.5 grams of benzoyl peroxide as the the organic peroxide to prepare a plastic paste.

In accordance with the procedures of Example 1, the paste was then measured in respect of its depth of curing, bending strength, discoloration, hardness and storage stability. The results are set forth in the table.

Comparison Example 3

As an example of the light polymerization type heretofore used in the prior art, a paste was obtained by mixing together 70 grams of a methyl methacrylate monomer and 30 grams of an aliphatic urethane dimethacrylate used as the polymerizable compounds having an ethylenically unsaturated double-bond, 0.5 grams of benzil dimethyl ketal and 0.05 grams of 1,2-benzanthraquinone as the photo-polymerization initiators, 0.5 grams of dimethylaminoethyl methacrylate as the reducing agent and 200 grams of cross-linked methyl methacrylate polymer as the filler.

In accordance with the procedures of Example 1, the paste was then measured in respect of its depth of curing, bending strength, discoloration, hardness and storage stability. The results are set forth in the table.

Comparison Example 4

In use, a formulation A obtained by mixing 70 grams of 2,2-bis[4-(2-hydroxy-3-methacryloxyphenyl)]propane and 30 grams of triethylene glycol dimethacrylate used as the polymerizable compounds having an ethylenically unsaturated double-bond with 0.5 grams of N,N'-dimethyl-p-toluidine as the reducing agent was blended at room temperature with a formulation B obtained by mixing 1.0 gram of benzoyl peroxide used as the organic peroxide with 100 grams of the filler that was finely divided silica surface-treated with 5 grams of γ-methacryloxypropyl trimethoxysilane to prepare a plastic paste.

In accordance with the procedures of Example 1, the paste was then measured in respect of its depth of curing, bending strength, discoloration, hardness and storage stability. The results are set forth in the table.

Comparison Example 5

As an example of the chemical polymerization type composite resins heretofore used in the art, a paste was prepared by mixing 70 grams of 2.2-bis[4-(2-hydroxy-3-methacryloxyphenyl)]propane and 30 grams of triethylene glycol dimethacrylate used as the polymerizable compounds having an ethylenically unsaturated double-bond with 100 grams of the filler, finely divided silica surface-treated with 5 grams of γ-methacryloxypropyl trimethoxysilane. The paste was then divided into two portions. A formulation C was obtained by adding to one portion 1.5 grams of N,N'-dimethyl-p-toluidine as the reducing agent, while a formulation D was obtained by additing to the other portion 1.5 grams of benzoyl peroxide as the organic peroxide. In use, the formulations C and D were blended together at room temperature to prepare a plastic paste. In accordance with the procedures of Example 1, that paste was examined with respect to its depth of curing, bending strength, discoloration, hardness and storage stability.

Comparison Example 6

As an example of the light polymerization type of composite resins heretofore used in the art, a plastic resin was obtained by mixing together 70 grams of 2,2-bis[4-(2-hydroxy-3-methacryloxyphenyl)]propane and 30 grams of triethylene glycol dimethacrylate used as the polymerizable compounds having an ethylenically unsaturated double-bond, 100 grams of finely divided silica—as the filler—surface-treated with 5 grams of γ-methacryloxypropyl trimethoxysilane, 0.5 grams of benzil-di(2-methoxyethyl)ketal and 0.2 grams of 2,4-diethylthioxanthone as the photo-polymerization initiators and 0.5 grams of triethanol amine as the reducing agent. In accordance with the procedures of Example 1, that paste was examined with respect to its depth of curing, bending strength, discoloration, hardness and storage stability.

Comparison Example 7

As an example of the light polymerization type opaque material heretofore used in the art, a paste was prepared by mixing together 50 grams of an aliphatic urethane dimethacrylate and 50 grams of trimethylol propane triacrylate used as the polymerizable compounds having an ethylenically unsaturated double-bond, 30 grams of finely divided silica and 70 grams of aluminum oxide surface-treated with 5 grams of γ-methacryloxypropyl trimethoxysilane as the filler, 0.5 grams of benzil dimethyl ketal and 0.2 grams of 2,4-diisopropylthioxantone as the photo-polymerization initiators, and 0.5 grams of 4-dimethylaminobenzoic acid ethyl ester and 0.5 grams of p-tolyldiethanol amine as the reducing agents.

In accordance with the procedures of Example 1, that paste was examined with respect to its depth of curing, bending strength, discoloration, hardness and storage stability.

TABLE

| | Example 1 | Example 2 | Example 3 | Example 4 | Example 5 | Example 6 | Example 7 | Example 8 | Example 9 |
|---|---|---|---|---|---|---|---|---|---|
| Photo-polymerization Initiator Amount (g) | Benzil dimethyl ketal 0.5 / 1,2-benzanthraquinone 0.05 | Benzil diethyl ketal 0.5 / 2-chlorothioxanthone 0.2 | 4,4'-dimethyl-benzildimethyl ketal 0.5 / Benzoin isobutyl ether 0.5 | Camphor quinone 0.2 | Benzil dimethyl ketal 0.5 / 1-chloroanthraquinone 0.1 | Benzil-di(2-methoxyethyl) ketal 0.5 / Thioxanthone 0.2 | Benzil dimethyl ketal 0.5 / Anthraquinone 0.1 | Benzil 0.2 | Benzil-di(2-methoxyethyl) ketal 0.5 / 2,4-diethylthioxanthone 0.2 |
| Reducing Agent Amount (g) | Dimethylaminoethyl methacrylate 0.5 | p-tolyldiethanolamine 0.5 | 4-dimethylamino benzoic acid methyl ester 0.5 | m-tolyldiethanolamine 0.5 | p-tolyldiethanolamine 0.5 | Dimethylaminoethyl methacrylate 0.5 / p-tolyldiethanolamine 0.5 | 4-dimethylamino benzoic acid methyl ester 0.5 | N,N'–dimethyl-p-toluidine 0.5 | Triethanolamine 0.5 |
| Organic Peroxide Amount (g) | Benzoyl peroxide 1.0 | Benzoyl peroxide 1.0 | Benzoyl peroxide 1.0 | Benzoyl peroxide 1.0 | Benzoyl peroxide 1.0 | Benzoyl peroxide 1.0 | Benzoyl peroxide 1.0 | Benzoyl peroxide 1.0 | Benzoyl peroxide 1.0 |
| Depth of Curing (mm) 30 sec. | 7.36 | 6.93 | 5.33 | 5.03 | 6.55 | 7.52 | 5.88 | 4.55 | 5.22 |
| 5 min. | 10.00 | 10.00 | 10.00 | 10.00 | 10.00 | 10.00 | 10.00 | 10.00 | 10.00 |
| Bending Strength (kg/cm²) | 713 | 709 | 732 | 651 | 699 | 745 | 1015 | 955 | 1137 |
| Discoloration | No substantial discoloration | No substantial discoloration | No substantial discoloration | No substantial discoloration | No substantial discoloration | No substantial discoloration | No substantial discoloration | No substantial discoloration | No substantial discoloration |
| Hardness (K.H.N.) Surface | 18.5 | 18.5 | 18.0 | 17.0 | 18.1 | 18.7 | 70.9 | 65.2 | 67.3 |
| 3 mm Below Surface | 18.3 | 18.5 | 18.0 | 17.0 | 18.0 | 18.7 | 70.8 | 65.0 | 67.3 |
| Storage Stability | Good | Good | Good | Good | Good | Good | Good | Good | Good |

| | Example 10 | Example 11 | Example 12 | Example 13 | Example 14 | Example 15 | Example 16 | Example 17 | Example 18 |
|---|---|---|---|---|---|---|---|---|---|
| Photo-polymerization Initiator Amount (g) | Benzil dimethyl ketal 0.5 / 2,4-diisopropylthioxanthone 0.2 | Benzil dimethyl ketal 0.5 / 1,2-benzanthraquinone 0.05 | Benzil dimethyl ketal 0.5 / Benzoin isobutyl ether 0.5 | Benzil diethyl ketal 0.5 / Thioxanthone 0.2 | Camphor quinone 0.2 | Benzil-di(2-methoxyethyl) ketal 0.5 / 1,2-benzanthraquinone 0.05 | Benzil dimethyl ketal 0.5 / 2-chlorothioxanthone 0.2 | Benzil dimethyl ketal 0.5 / Anthraquinone 0.1 | Benzil 0.2 |
| Reducing Agent Amount (g) | 4-dimethylamino benzoic acid ethyl ester 0.5 / p-tolyldiethanolamine 0.5 | 4-dimethylamino benzoic acid methyl ester 0.5 / m-tolyldiethanolamine 0.5 | Dimethylaminoethyl methacrylate 0.5 | 4-dimethylamino benzoic acid ethyl ester 0.5 | Triethanolamine 0.5 | 4-dimethylamino benzoic acid ethyl ester 0.5 / p-tolyldiethanolamine 0.5 | Dimethylaminoethyl methacrylate 0.5 | N,N'–dimethyl-p-toluidine 0.5 | p-tolyldiethanolamine 0.5 |
| Organic Peroxide Amount (g) | Benzoyl peroxide 1.0 | Benzoyl peroxide 1.0 | Benzoyl peroxide 1.0 | Benzoyl peroxide 1.0 | Benzoyl peroxide 1.0 | Benzoyl peroxide 1.0 | Benzoyl peroxide 1.0 | Benzoyl peroxide 1.0 | Benzoyl peroxide 1.0 |
| Depth of Curing (mm) 30 sec. | 1.83 | 6.43 | 6.22 | 6.87 | 5.31 | 5.92 | 5.87 | 7.11 | 5.22 |
| 5 min. | 10.00 | 10.00 | 10.00 | 10.00 | 10.00 | 10.00 | 10.00 | 10.00 | 10.00 |
| Bending Strength (kg/cm²) | 980 | 705 | 754 | 720 | 873 | 903 | 751 | 732 | 685 |
| Discoloration | No substantial discoloration | No substantial discoloration | No substantial discoloration | No substantial discoloration | No substantial discoloration | No substantial discoloration | No substantial discoloration | No substantial discoloration | No substantial discoloration |
| Hardness (K.H.N.) Surface | 70.2 | 11.7 | 11.9 | 18.0 | 22.5 | 67.3 | 18.3 | 17.9 | 11.3 |

TABLE-continued

| | Example 19 | Example 20 | Comparison Example 1 | Comparison Example 2 | Comparison Example 3 | Comparison Example 4 | Comparison Example 5 | Comparison Example 6 | Comparison Example 7 |
|---|---|---|---|---|---|---|---|---|---|
| Photo-polymerization Initiator Amount (g) | Benzil dimethyl ketal 0.5 1,2-benzathraquinone 0.05 | Benzil-di(2-methoxyethyl) ketal 0.5 2-chlorothioxanthone 0.2 | — | — | Benzil dimethyl ketal 0.5 1,2-benzanthraquinone 0.05 | — | — | Benzil-di(2-methoxyethyl) ketal 0.5 2,4-diethylthioxanthone 0.2 | Benzil dimethyl ketal 0.5 2,4-diisopropylthioxanthone 0.2 |
| Reducing Agent Amount (g) | 4-dimethylamino benzoic acid ethyl ester 0.5 | 4-dimethylamino benzoic acid ethyl ester 0.5 p-tolyldiethanolamine 0.5 | p-tolyldiethanol amine 0.5 | p-tolyldiethanolamine 1.5 | Dimethylaminoethyl methacrylate 0.5 | N,N'—dimethyl-p-toluidine 0.5 | N,N'—dimethyl-p-toluidine 1.5 | Triethanolamine 0.5 | 4-dimethylamino benzoic acid ethyl ester 0.5 p-tolyldiethanolamine 0.5 |
| Organic peroxide Amount (g) | Benzoyl peroxide 1.0 | Benzoyl peroxide 1.0 | Benzoyl peroxide 1.0 | Benzoyl peroxide 1.5 | — | Benzoyl peroxide 1.0 | Benzoyl peroxide 1.5 | — | — |
| Depth of Curing (mm) | | | | | | | | | |
| 30 sec. | 7.27 | 5.77 | — | — | 4.80 | — | — | 3.75 | 1.32 |
| 5 min. | 10.00 | 10.00 | Uncured | 10.00 | 4.80 | Uncured | 10.00 | 3.75 | 1.32 |
| Bending Strength (kg/cm²) | 690 | 1019 | Unmeasurable | 615 | 601 | Unmeasurable | 870 | 824 | Unmeasurable |
| Discoloration | No substantial discoloration | No substantial discoloration | — | Turning to Brown | No substantial discoloration | — | Turning to Brown | No substantial discoloration | No substantial discoloration |
| Hardness (K.H.N.) | | | | | | | | | |
| Surface | 17.3 | 63.6 | Unmeasurable | 13.8 | 14.0 | Unmeasurable | 60.5 | 61.3 | 60.0 |
| 3 mm Below Surface | 17.4 | 63.6 | Unmeasurable | 13.7 | 8.3 | Unmeasurable | 60.3 | 37.9 | Unmeasurable |
| Storage Stability | Good | Good | Good | Formulation [A] Discoloration | Good | Good | Formulation [C] Discoloration Formulation [D] Curing | Good | Good |
| 3 mm Below Surface Storage stability | 70.0 Good | 11.7 Good | 11.8 Good | 18.0 Good | 22.4 Good | 67.3 Good | 18.4 Good | 17.9 Good | 11.3 Good |

It was found (from comparison of Examples 2 and 8 with Comparison Examples 1 and 4 in particular) that the invented compositions for dental restoration were improved in respect of the depth of curing, bending strength, discoloration and hardness over those containing the same composition of monomer and filler but freed of any photo-polymerization initiator. It was also found (from comparison of Examples 2 and 8 with Comparison Examples 2 and 5, respectively) that the invented compositions were improved in respect of the curing time over the formations in which the amounts of the reducing agent and organic peroxide were increased so as to obtain the curing time at about 3 minutes as the chemical polymerization type, and excelled in the discoloration, storage stability and bending strength owing to the fact that the amount of the reducing agent added was reduced.

It was further noted (from comparison of Examples 1 and 9 with Comparison Examples 3 and 6) that the invented compositions were improved in respect of the curing property over the prior art chemical polymerization type compositions having the same composition of monomer and filler but freed of any organic peroxide, since they were found to be cured more deeply for an irradiation time of as short as 30 seconds by the addition of the organic peroxide, and the samples were completely cured as a whole after the lapse of 5 minutes. A higher bending strength was also obtained. Even an example (Example 10 and Comparison Example 7) of the opaque material having poor light transmitting properties were improved in respect of the curing property by short-time manipulation.

It has thus been ascertained that the invented compositions for dental restoration excel in the curing property, manipulation property and storage stability, and provide cured products having improved properties.

What is claimed is:

1. A combined chemical-/light-polymerization type composition for dental restoration consisting of a formulation A consisting essentially of (a) an ethylenically polymerizable unsaturated compound, (b) a photo-polymerization initiator and (c) a reducing agent, and a formulation B consisting essentially of (d) a filler and (e) an organic peroxide, said formulations A and B being separately packaged and designed to be mixed for use, wherein said photo-polymerization initiator consists of one or two or more ketal base compounds expressed in terms of the following general formula I:

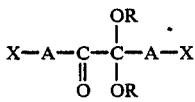

wherein
X is H, Cl, an alkyl group having 1 to 5 carbon atoms or an alkoxy group having 1 to 5 carbon atoms,
A is a six-membered aromatic group, and
R is an alkyl group having 1 to 10 carbon atoms, an aralkyl group having 7 to 9 carbon atoms or a $$-(C_nH_{2n}O)_{\overline{m}}R'$$

in which n is an integer of 2 to 5, m is an integer of 1 to 5 and R' is an alkyl group having 1 to 5 carbon atoms, and any one or combination of anthraquinone, 1-chloroanthraquinone and 1,2-benzanthraquinone.

2. The composition as defined in claim 1, wherein said ethylenically polymerizable unsaturated compound is one or two or more compounds having one ethylenically unsaturated double-bond.

3. The composition as defined in claim 1, wherein said ethylenically polymerizable unsaturated compound is one or two or more compounds having at least two ethylenically unsaturated double-bonds.

4. The composition as defined in claim 1, wherein said ethylenically polymerizable unsaturated compound comprises a mixture of the compound having one ethylenically unsaturated double-bond with that having at least two ethylenically unsaturated double-bonds.

5. The composition as defined in any one of claims 1, wherein said ethylenically polymerizable unsaturated compound is one or two or more compounds selected from the group consisting of methacrylates and acrylates.

6. The composition as defined in claim 1, wherein the ketal base compound having the general formula 1 are any one benzil dimethyl ketal, benzil diethyl ketal, benzil-di(2-methoxyethyl)ketal and 4,4-dimethylbenzildimethyl ketal.

7. The composition as defined in claim 1, wherein the concentration of the ketal base compound having the general formula 1 is 0.01 to 5 weight % with respect to the ethylenically polymerizable unsaturated compound.

8. The compositions as defined in claim 1, wherein the concentration of the anthraquinone base compound of the general formula 2 is 0.01 to 5 weight % with respect to the ethylenically polymerizable unsaturated compound.

9. The composition as defined in claim 1, wherein the reducing agent is any one or combinations of p-tolyl diethanolamine, m-tolyldiethanolamine, N,N'-dimethyl-p-toluidine, dimethylaminoethyl methacrylate, triethanolamine, 4-dimethylaminobenzoic acid methyl ester and 4-dimethylaminobenzoic acid ethyl ester.

10. The composition as defined in claim 1, wherein the concentration of the reducing agent is 0.01 to 5 weight % with respect to the ethylenically polymerizable unsaturated compound.

11. The composition as defined in claim 1, wherein the filler is inorganic, organic, and/or composite thereof.

12. The composition as defined in claim 1, wherein the organic peroxide is benzoyl peroxide.

13. The composition as defined in claim 1, wherein the concentration of the organic peroxide is 0.01 to 5 weight % with respect to the filler.

14. The composition as defined in claim 1 wherein the amount of the ethylenically polymerizable unsaturated compound is between 90 weight % and 10 weight % with respect to the filler.

* * * * *